(12) United States Patent
Bargon et al.

(10) Patent No.: US 11,246,652 B2
(45) Date of Patent: Feb. 15, 2022

(54) SURGICAL TISSUE FUSION INSTRUMENT AND SUPPORT STRUCTURE FOR SAME

(71) Applicant: Aesculap AG, Tuttlingen (DE)

(72) Inventors: Rainer Bargon, Tuttlingen (DE); Bernd Blender, Mühlheim a. d. Donau (DE); Stefan Eick, Tuttlingen (DE); Nikolaus Hafner, Tuttlingen (DE); Patrick Heizmann, Hüfingen (DE); Eugen Herner, Villingen-Schwenningen (DE); Christian Huber, Mühlheim (DE); Christof Merckle, Mannheim (DE); Erich Odermatt, Schaffhausen (CH); Christoph Rothweiler, Donaueschingen (DE)

(73) Assignee: AESCULAP AG, Tuttlingen (DE)

( * ) Notice: Subject to any disclaimer, the term of this patent is extended or adjusted under 35 U.S.C. 154(b) by 186 days.

(21) Appl. No.: 15/505,841

(22) PCT Filed: Mar. 18, 2016

(86) PCT No.: PCT/EP2016/055990
§ 371 (c)(1),
(2) Date: Feb. 22, 2017

(87) PCT Pub. No.: WO2016/150861
PCT Pub. Date: Sep. 29, 2016

(65) Prior Publication Data
US 2018/0214201 A1 Aug. 2, 2018

(30) Foreign Application Priority Data

Mar. 20, 2015 (DE) .......................... 102015205056.4

(51) Int. Cl.
*A61B 18/14* (2006.01)
*A61B 17/11* (2006.01)
(Continued)

(52) U.S. Cl.
CPC .......... *A61B 18/1485* (2013.01); *A61B 17/11* (2013.01); *A61B 17/1114* (2013.01);
(Continued)

(58) Field of Classification Search
CPC ............ A61B 18/1445; A61B 17/1114; A61B 18/1485; A61B 18/1402
See application file for complete search history.

(56) References Cited

U.S. PATENT DOCUMENTS 9,364,229 B2 * 6/2016 D'Agostino ..... A61B 17/07292
2004/0143263 A1 7/2004 Schechter et al.
(Continued)

FOREIGN PATENT DOCUMENTS

WO 20080082444 7/2008

OTHER PUBLICATIONS

Beitz W. et al.: DUBBEL—Taschenbuch fur den Maschinenbau, Band 1, 18. Auflage, ISBN 978-3-662-06774-1 (eBook); https://doi.org/10.1007/978-3-662-06774-1_6.

*Primary Examiner* — Michael F Peffley
*Assistant Examiner* — Bo Ouyang
(74) *Attorney, Agent, or Firm* — Lewis Kohn & Walker LLP; David M. Kohn

(57) ABSTRACT

Surgical tissue fusion instrument and support structure having two gripping structures which are movable relative to each other and which are designed to bring together biological tissue sections that are to be connected to each other, with heat-generating means which are assigned to the gripping structures and, during tissue fusion, cause heat to be introduced in the area of a connection site of the biological tissue sections, and also with a support structure which is held between the gripping structures and, during tissue fusion, is operatively connected to the tissue sections. The (Continued)

support structure has at least one additional physical functional structure for aiding or promoting the tissue fusion.

10 Claims, 7 Drawing Sheets

(51) Int. Cl.
*A61B 17/00* (2006.01)
*A61B 18/00* (2006.01)
*A61B 17/072* (2006.01)
*A61B 17/115* (2006.01)

(52) U.S. Cl.
CPC .... *A61B 18/1402* (2013.01); *A61B 17/07292* (2013.01); *A61B 17/1155* (2013.01); *A61B 18/1445* (2013.01); *A61B 2017/00504* (2013.01); *A61B 2017/00867* (2013.01); *A61B 2017/00884* (2013.01); *A61B 2017/00889* (2013.01); *A61B 2017/00893* (2013.01); *A61B 2017/00955* (2013.01); *A61B 2017/1132* (2013.01); *A61B 2018/0063* (2013.01); *A61B 2018/00196* (2013.01); *A61B 2018/00619* (2013.01); *A61B 2018/145* (2013.01)

(56) References Cited

U.S. PATENT DOCUMENTS

| | | | |
|---|---|---|---|
| 2004/0210282 A1 | 10/2004 | Flock et al. | |
| 2005/0021026 A1 | 1/2005 | Baily | |
| 2005/0059997 A1 | 3/2005 | Bauman et al. | |
| 2006/0085034 A1* | 4/2006 | Bettuchi | A61B 17/115 606/219 |
| 2012/0022531 A1 | 1/2012 | Winter | |
| 2013/0090645 A1* | 4/2013 | Weisshaupt | A61B 17/1114 606/40 |
| 2014/0142561 A1* | 5/2014 | Reu | A61B 18/082 606/29 |
| 2014/0309634 A1* | 10/2014 | Weisshaupt | A61B 17/1155 606/49 |

* cited by examiner

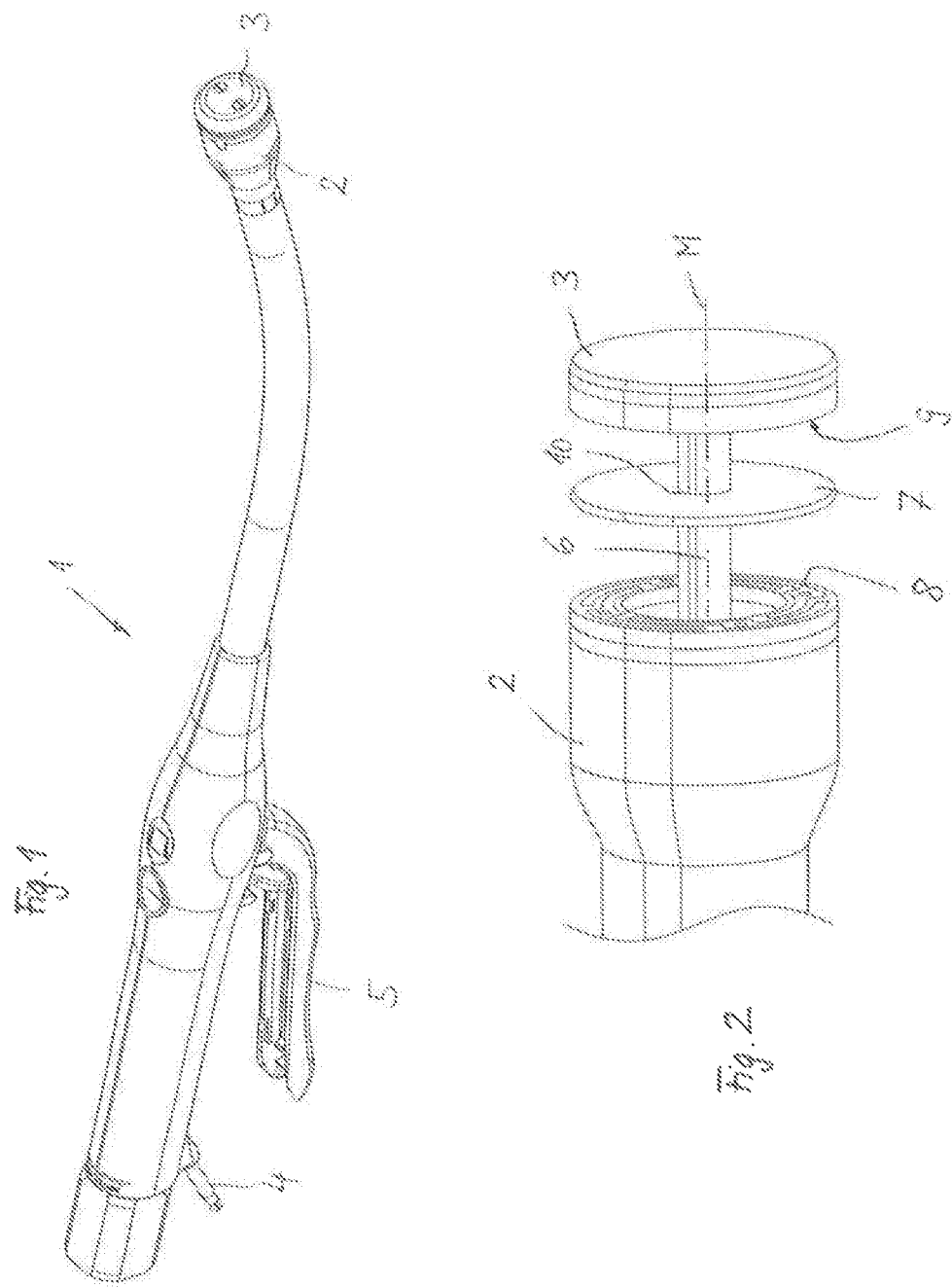

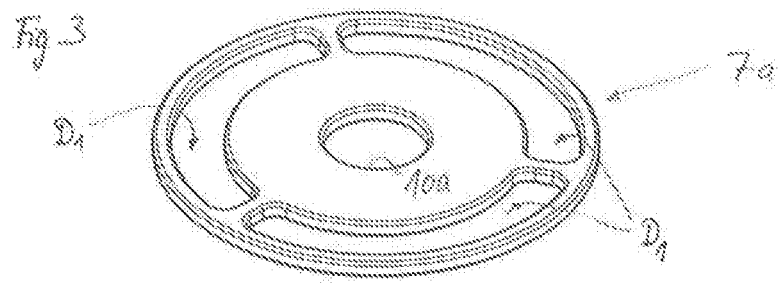
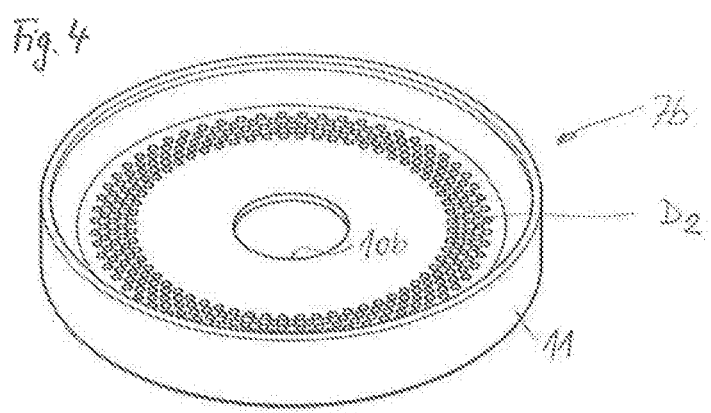
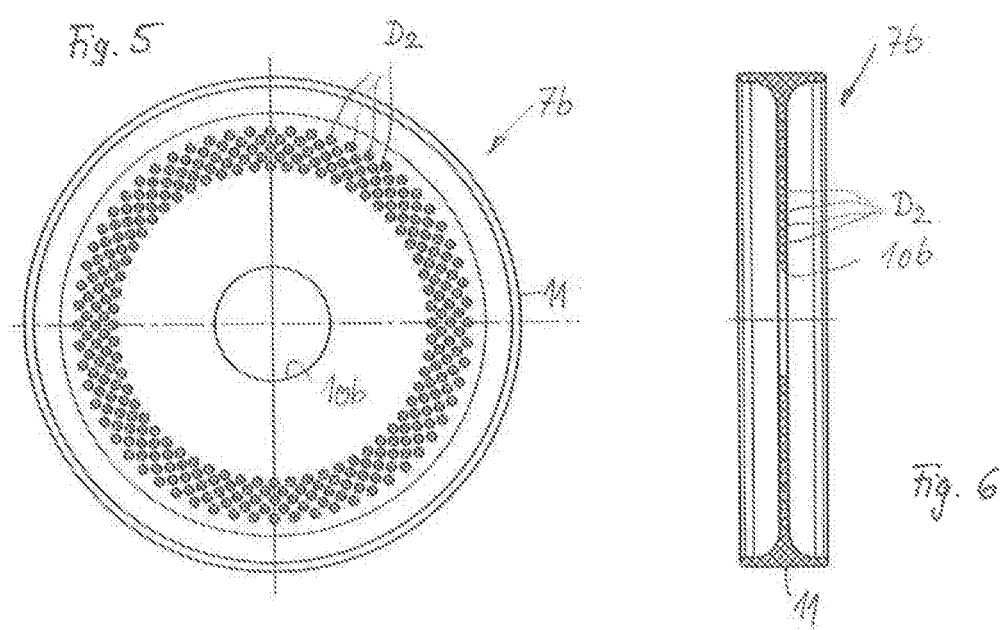

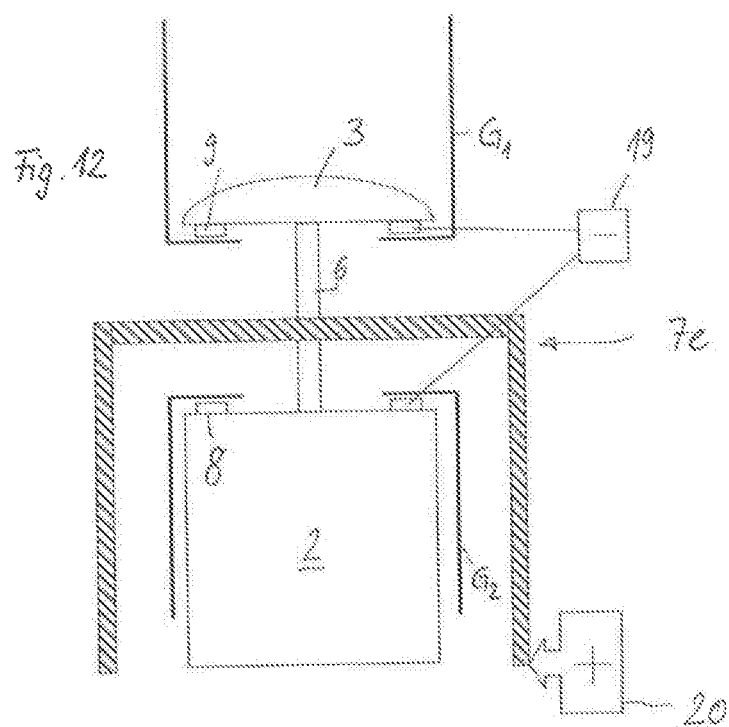
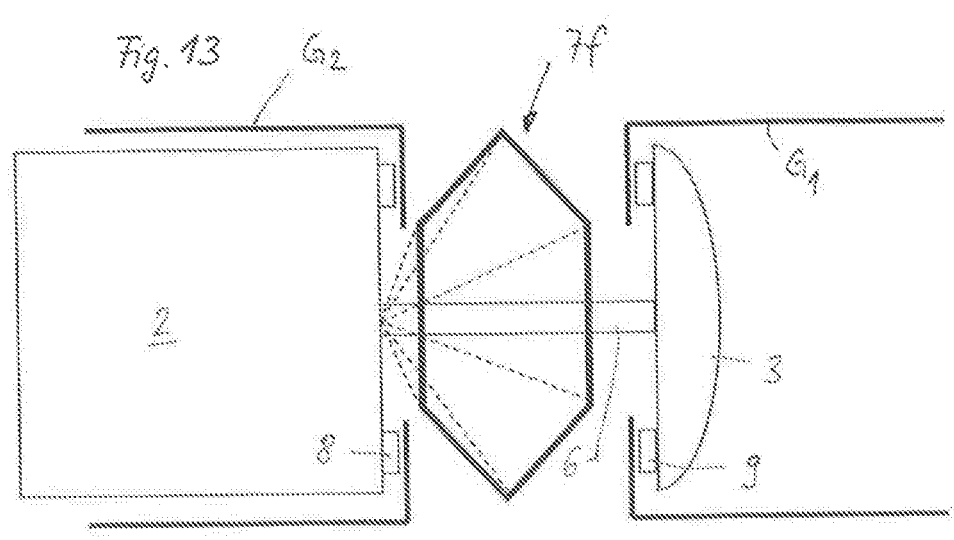

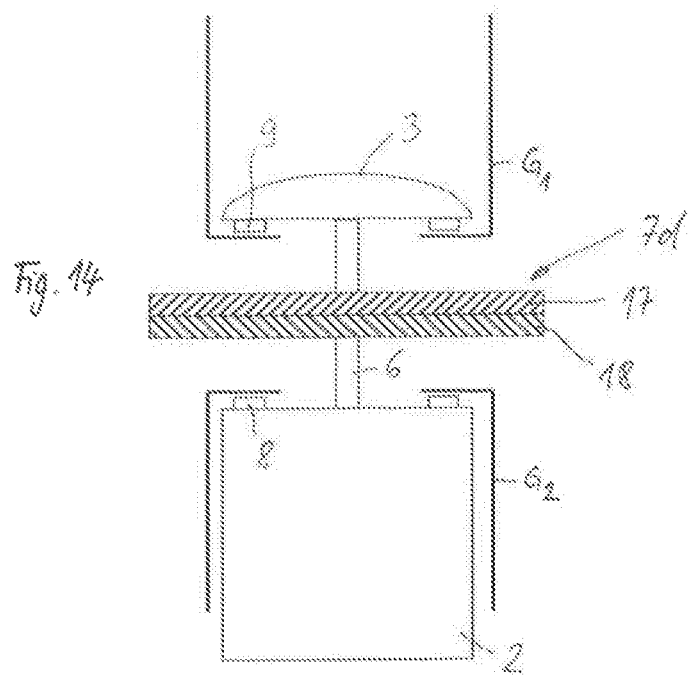
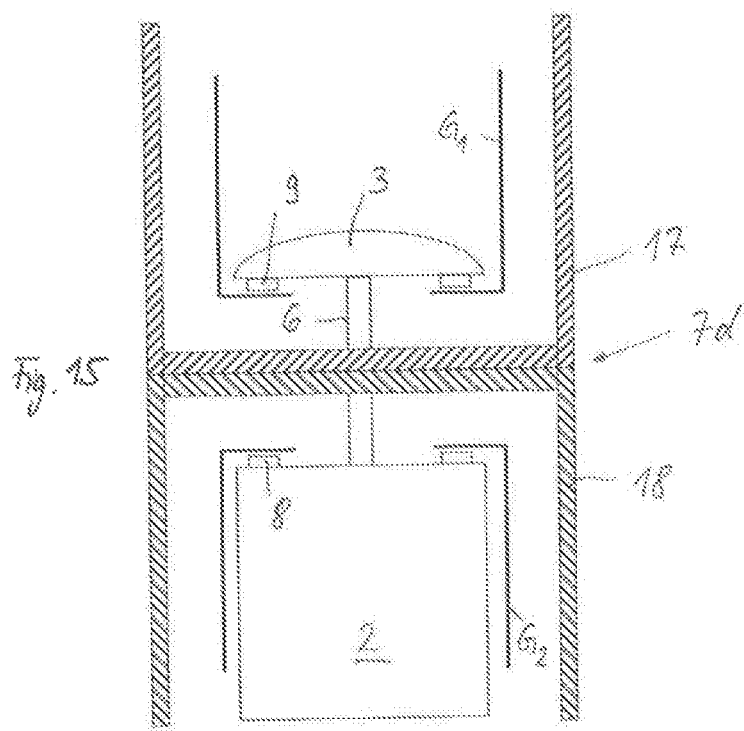

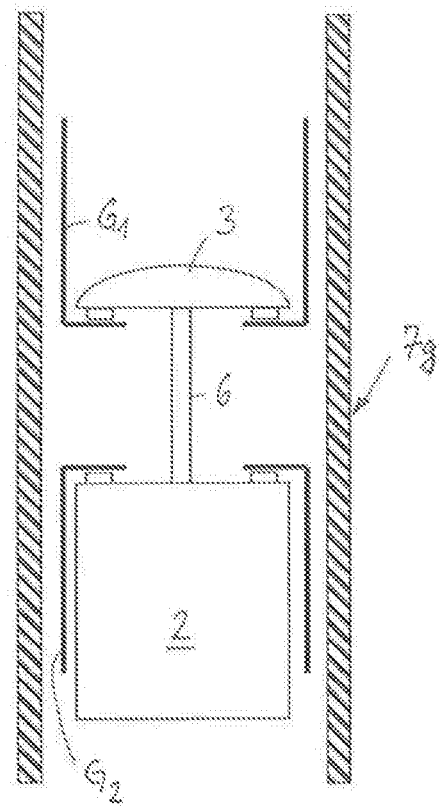 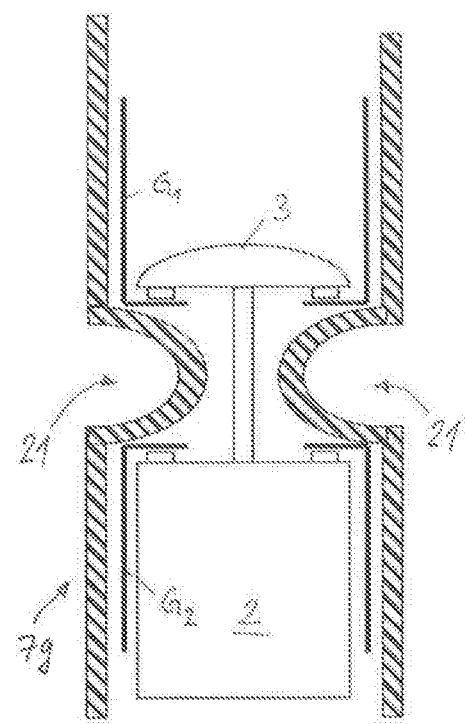

SURGICAL TISSUE FUSION INSTRUMENT AND SUPPORT STRUCTURE FOR SAME

This application is a United States National Stage Application claiming the benefit of priority under 35 U.S.C. 371 from International Patent Application No. PCT/EP2016/055990 filed Mar. 18, 2016, which claims the benefit of priority from German Patent Application Serial No. DE 102015205056.4 filed Mar. 20, 2015, the entire contents of which are herein incorporated by reference.

The invention relates to a surgical tissue fusion instrument with two gripping structures which are movable relative to each other and which are designed to bring together biological tissue sections that are to be connected to each other, with heat-generating means which are assigned to the gripping structures and, during tissue fusion, cause heat to be introduced in the area of a connection site of the biological tissue sections, and also with a support structure which is assigned to the gripping structures and, during tissue fusion, is operatively connected to the tissue sections, and also a support structure for a surgical tissue fusion instrument of this kind.

A surgical tissue fusion instrument of this kind is known from DE 10 2010 020 664 A1. The tissue fusion instrument is designed as a circular instrument with an anvil part, which is linearly movable in a base part. The anvil part and an instrument head of the base part have contact faces which are directed toward each other and to which electrode arrangements are assigned in order to be able to apply heat to biological tissue sections clamped between the contact faces, said heat bringing about tissue fusion of the biological tissue sections. Between the mutually opposite contact faces of the anvil part and of the instrument head of the base part, a disk that annularly surrounds an anvil shaft of the anvil part is arranged as a support structure. The disk represents a support structure which is positioned between the biological tissue sections during tissue fusion and which is made from a material that aids or promotes the tissue connection and that is medically compatible.

The object of the invention is to make available a surgical tissue fusion instrument and a support structure which are of the type mentioned at the outset and which permit a further improved connection of the biological tissue sections to each other.

This object is achieved by the fact that the support structure has at least one physical functional structure, in particular at least one additional physical functional structure, for aiding or promoting the tissue fusion. The surgical tissue fusion instrument according to the invention creates a cohesive connection between the biological tissue sections, preferably exclusively by structural changes of the biological material of the tissue sections, i.e. in particular without additional mechanical connecting means such as staples or sutures. Accordingly, the tissue fusion instrument according to the invention preferably permits staple-free tissue fusion. The support structure can be used in linear tissue fusion instruments and also in circular tissue fusion instruments. According to the invention, provision can also be made that a tissue fusion instrument is additionally provided with a staple application function in order to aid the tissue connection by means of a stapled suture generated mechanically by staples. The support structure can particularly advantageously be used in a circular tissue fusion instrument for connecting biological tissue sections formed as hollow organs.

The support structure has a medically compatible material or is produced from a medically compatible material and aids or promotes the tissue fusion between the tissue sections. In preferred embodiments, the support structure can be resorbable. In addition, the support structure has at least one further physical functional structure, which improves the connection of the tissue sections. The physical functional structure can be purely mechanical. Alternatively or in addition, it can have physical or chemical properties, which can be activated depending on environmental or functional parameters.

The medically compatible material mentioned in the previous paragraph can be chosen from the group comprising or consisting of synthetic polymer, biopolymer (naturally occurring polymer), technical biopolymer (industrially produced biopolymer), protein, extracellular protein, serum protein, glycoprotein, polyamino acid, polyhomoamino acid, polyheteroamino acid, polysaccharide, mucopolysaccharide and mixtures thereof.

The synthetic polymer can in principle be a resorbable polymer or a non-resorbable polymer. A preferred resorbable polymer can be chosen, for example, from the group comprising or consisting of polyglycolide, polylactide, polytrimethylene carbonate, poly-$\varepsilon$-caprolactone, poly-3-hydroxybutyrate, poly-4-hydroxybutyrate, poly-5-hydroxybutyrate, poly-6-hydroxybutyrate and mixtures thereof. A preferred non-resorbable polymer is a fluorinated polymer, in particular a perfluorinated polymer, for example polytetrafluoroethylene.

The protein can be chosen from the group comprising or consisting of collagen, gelatin, elastin, reticulin, laminin, fibronectin, fibrillin, albumin, derivatives thereof, peptide fragments thereof, subunits thereof and mixtures thereof.

The protein can in particular be collagen, which is chosen from the group comprising or consisting of type I collagen, type II collagen, type III collagen, type VI collagen, derivatives thereof, peptide fragments thereof, subunits thereof and mixtures thereof.

The polysaccharide can be chosen from the group comprising or consisting of starch, modified starch, amylose, amylopectin, dextran, hyaluronic acid, heparin, heparan sulfate, chondroitin-4-sulfate, chondroitin-6-sulfate, dermatan sulfate, keratan sulfate, derivatives thereof and mixtures thereof.

In an embodiment of the invention, the physical functional structure has apertures or material weakenings in the support structure, which are positioned in areas where the heat introduced by the heat-generating means passes through the support structure and the tissue sections. The heat generated in the area of the connection site of the biological tissue sections generates a desired cohesive connection between the tissue sections in the manner of a weld. The apertures or material weakenings in the support structure lead, in these areas, to an improved passage of energy radiation on the one hand and, moreover, to direct contacting of the tissue sections in the area of the apertures, if the support structure is positioned between the tissue sections. The heat-generating means are to be understood as all types of energy input means which either deliver thermal energy directly to the connection site or deliver the energy waves which, at the connection site itself, lead to heat generation in the at least one tissue section. The heat-generating means provided are in particular high-frequency or radio-frequency electrodes, which are integrated in the gripping structures. Alternatively, laser units, sonotrodes, microwave generators, plasma generators, resistance heaters such as cauters or a combination of two or more of said heat-generating means, can be provided as heat-generating means and integrated in the gripping structures.

In a further embodiment of the invention, the apertures are designed as linearly or circularly extending oblong holes. The extent of the apertures is correspondingly adapted depending on whether the tissue fusion instrument is designed as a linear or circular instrument.

In a further embodiment of the invention, the apertures are designed as perforations. The perforations form a multiplicity of small holes distributed uniformly across the corresponding areas of the support structure.

In a further embodiment of the invention, the physical functional structure is configured as an edge web which extends in the direction of movement of the gripping structures and which externally flanks the area of the connection site of the tissue sections. In the case of a disk-shaped or ring-shaped support structure, the edge web is provided annularly on the outer edge of the support structure and stiffens and supports the tissue sections connected to each other, in particular biological hollow organs connected to each other.

In a further embodiment of the invention, the physical functional structure comprises at least one storage space for accommodating a liquid or flowable additive. The physical functional structure preferably comprises at least one storage space containing a liquid or flowable additive. The at least one storage space is integrated in the support structure. Corresponding walls of the storage space that face toward the gripping structures preferably tear open as soon as the gripping structures are brought together for activation of a tissue fusion procedure.

In a further embodiment of the invention, the physical functional structure has profiles, particularly in the form of polygonal or angular protuberances or indentations, which are provided on at least one end face of the support structure directed toward a gripping structure. The profiles improve the connection of the support structure to at least one tissue section. Moreover, the profiles can be provided in such a way as to deform when the gripping structures apply pressure in the area of the at least one end face of the support structure, and to cause the support structure to tear open, as a result of which in particular a liquid or flowable additive is released from at least one storage space. Depending on the design, this leads to the additive being applied on one side or on both sides of the at least one tissue section.

Within the meaning of the present invention, the term "additive" can denote an additive (singular) or a number of additives (plural), i.e. two or more additives.

The additive is preferably stored in a liquid form, in particular as a solution, suspension or emulsion, preferably as an aqueous solution, aqueous suspension or aqueous emulsion, or in a flowable form, i.e. in particular in the form of particles, a paste, a melt or gel, preferably a hydrogel. In this way, the additive is able to flow in, during the introduction of heat during a tissue fusion procedure in the area of the tissue sections that are to be connected, in particular under the effect of pressure and/or temperature.

The additive can be chosen from the group comprising or consisting of salt, for example inorganic salt, wax, fat, fatty acid, alcohol, synthetic polymer, biopolymer (naturally occurring polymer), technical biopolymer (industrially produced biopolymer), protein, extracellular protein, serum protein, glycoprotein, polyamino acid, polyhomoamino acid, polyheteroamino acid, oligopeptide, amino acid, polysaccharide, mucopolysaccharide, oligosaccharide, monosaccharide, lipid, glycolipid, medicament, medical or pharmaceutical active substance, growth factor, cyanoacrylate and mixtures thereof.

The salt can be chosen from the group comprising or consisting of alkali metal halide, alkaline earth metal halide, phosphate, alkali metal phosphate, alkaline earth metal phosphate and mixtures thereof.

The salt can in particular be chosen from the group comprising or consisting of sodium chloride, potassium chloride, barium chloride, magnesium chloride, calcium chloride, sodium phosphate, potassium phosphate, barium phosphate, magnesium phosphate, calcium phosphate, mixed phosphates thereof and mixtures thereof.

The synthetic polymer can be chosen, for example, from the group comprising or consisting of polyglycolide, polylactide, polytrimethylene carbonate, poly-ε-caprolactone, poly-3-hydroxybutyrate, poly-4-hydroxybutyrate, poly-5-hydroxybutyrate, poly-6-hydroxybutyrate and mixtures thereof.

The protein can be chosen from the group comprising or consisting of collagen, gelatin, elastin, reticulin, laminin, fibronectin, fibrillin, albumin, derivatives thereof, peptide fragments thereof, subunits thereof and mixtures thereof.

The protein can in particular be collagen, which is chosen from the group comprising or consisting of type I collagen, type II collagen, type III collagen, type VI collagen, derivatives thereof, peptide fragments thereof, subunits thereof and mixtures thereof.

The polysaccharide can be chosen from the group comprising or consisting of starch, modified starch, amylose, amylopectin, dextran, hyaluronic acid, heparin, heparan sulfate, chondroitin-4-sulfate, chondroitin-6-sulfate, dermatan sulfate, keratan sulfate, derivatives thereof and mixtures thereof.

The medicament can be chosen from the group comprising or consisting of antibiotics, cytostatics, spasmolytics, platelet aggregation inhibitors, anticoagulants, hormones, gastrointestinal therapeutics, local anesthetics, antihypertensives, anti-inflammatories, analgesics and mixtures thereof.

The medical or pharmaceutical active substance can be chosen from the group comprising or consisting of antimicrobial, in particular antibiotic, active substance, hemostyptic active substance, anti-inflammatory active substance, active substance that promotes wound healing, analgesic active substance, growth-promoting active substance and mixtures thereof.

The antimicrobial active substance can be chosen from the group comprising or consisting of silver, silver salt, antibiotic, polyhexamethylene biguanide and mixtures thereof.

The growth factor can be chosen from the group comprising or consisting of fibroblast growth factor (FGF), transforming growth factor (TGF), platelet-derived growth factor (PDGF), epidermal growth factor (EGF), granulocyte-macrophage colony stimulating factor (GMCSF), vascular endothelial growth factor (VEGF), insulin-like growth factor (IGF), hepatocyte growth factor (HGF), interleukin, nerve growth factor (NGF), hematopoetic growth factor and mixtures thereof.

In a further embodiment of the invention, the additive is an additive that improves tissue contact. In particular, the additive can be an additive that is designed to improve the tissue contact to a sensor or to a sensor arrangement of the surgical tissue fusion instrument. An additive of this kind can in particular be an immersion medium, for example glycerol, hydrogels or oils with a defined refractive index.

In a further embodiment of the invention, the additive is an additive that is designed to improve an image-based evaluation of the biological tissue sections to be connected to each other or of biological tissue sections already connected to each other. A suitable additive can in particular be designed as contact material for better coupling-in of ultrasound, for example, to permit image-based evaluation. Suitable additives are, for example, hydrogels of carbomers or derivatives thereof, plant lipogels (oleogels), synthetic lipogels (oleogels), mineral lipogels (oleogels), hyaluronic acid or biological gels such as aloe vera.

In a further embodiment of the invention, the additive is an additive that is designed to improve the input of energy and thus the input of heat into the biological tissue sections to be connected to each other. A suitable additive is, for example, in the form of glycerol, biological oils, synthetic oils, mineral oils, hydrogels or lipogels (oleogels).

In a further embodiment of the invention, the additive is an energy-converting or energy-absorbing additive that is designed to bring about a positioned conversion from one energy form, for example light energy, to thermal energy. A suitable additive can be, for example, in the form of metallic or metallized particles such as silver particles, carbon particles or other absorbing materials or nanostructures. The additive can be applied in the form of particles, emulsions, melts or in a dissolved form.

In a further embodiment of the invention, the additive is an energy-coupling additive that is designed in particular to introduce inductive energy. Such an additive can, for example, be in the form of ferromagnetic particles, graphite or carbon-containing materials.

In a further embodiment of the invention, the additive is a tissue-structure-labelling additive that is designed for labelling the biological tissue sections to be connected to each other or biological tissue sections already connected to each other. A suitable additive can be, for example, a fluorescence dye. The use of fluorescence dyes has in particular the advantage that the structure of the tissue sections can be detected by means of an optical sensor arrangement contained in the surgical tissue fusion instrument.

In a further embodiment of the invention, the additive is a tissue-density-labelling additive that is designed for labelling the density of the biological tissue sections to be connected to each other or of biological tissue sections already connected to each other, for example by means of ultrasound. A suitable additive, for example, is in the form of gas-filled microbubbles.

In a further embodiment of the invention, the additive is an X-ray contrast medium, for example barium sulfate, or an iodine-containing contrast medium. A particular advantage of this is that it permits an image-based evaluation of the biological tissue sections to be connected to each other or of biological tissue sections already connected to each other.

In a further embodiment of the invention, the physical functional structure is formed by a shape-change structure, which can be activated according to a change of at least one physical or chemical environmental parameter. The shape-change structure can be provided by a shape-memory structure, by a sponge-like structure, in the form of a heat-shrink sleeve, or in some other way. As long as the shape-change structure is not activated, the support structure has a constant and stable shape.

In a further embodiment of the invention, a change of temperature and/or change of water content acting on the functional structure is provided as the change of environmental parameters. Accordingly, a corresponding activation can be effected by introduction of heat or also by delivery of liquid to the support structure.

In a further embodiment of the invention, the physical functional structure is designed to be electrically conductive at least in parts. If the functional structure is electrically conductive, said functional structure can also be designed as an electrical pole for electrical activation of the energy input by the heat-generating means. In this embodiment, it suffices if one of the two gripping structures forms the other electrical pole in order to permit a flow of electrical energy upon activation. The delivery of electrical energy can also bring about a desired change of shape of the functional structure, if the functional structure is designed as a shape-change structure.

In a further embodiment of the invention, the support structure is designed as a hollow body which is open at one or both ends and which at least in part encloses the outside of at least one tissue section in the form of a hollow organ. In a further embodiment, the shape-change structure has a heat-shrink sleeve function. In this embodiment, the support structure can provide the hollow organs with external support and ensure a secure and tight connection between these hollow organs.

In a further embodiment of the invention, the surgical tissue fusion instrument has a sensor or a sensor arrangement. The sensor or the sensor arrangement can be an electronic sensor or an electronic sensor arrangement, a temperature sensor or a temperature sensor arrangement or an optical sensor, in particular a spectroscopic sensor, or an optical sensor arrangement, in particular a spectroscopic sensor arrangement. The sensor or the sensor arrangement is preferably integrated in a handle of the surgical tissue fusion instrument.

In a further embodiment of the invention, the surgical tissue fusion instrument has an energy source, in particular a current generator, preferably a high-frequency current generator, a radio-frequency generator, an ultrasonic wave generator, a microwave generator or a light source, in particular a laser. The energy source is preferably integrated in a handle of the surgical tissue fusion instrument.

In a further embodiment of the invention, the surgical tissue fusion instrument has an energy-transmitting means that is designed to transmit energy from an energy source of the surgical tissue fusion instrument to at least one of the two gripping structures, in particular to both gripping structures, preferably to the one or more heat-generating means. The energy-transmitting element can, for example, be in the form of electrical lines or light guides, i.e. transparent components such as fibers, tubes or rods, which can transport light over short or long distances.

In a further embodiment of the invention, the surgical tissue fusion instrument has an accumulator. The accumulator is designed to supply current to the tissue fusion instrument, in particular to an energy source integrated therein. The accumulator can in principle be an accumulator cell or an accumulator pack. The accumulator is preferably (likewise) integrated in a handle of the surgical tissue fusion instrument.

For the support structure, the object of the invention is achieved by the fact that at least one physical functional structure, in particular at least one additional physical functional structure, is provided to aid and promote a connection of the biological tissue sections, as have been described above.

Further advantages and features of the invention will become clear from the claims and also from the following description of preferred exemplary embodiments of the invention that are shown in the drawings.

FIG. 1 shows a perspective view of an embodiment of a surgical tissue fusion instrument according to the invention in a circular form.

FIG. 2 shows an enlarged view of a head area of the tissue fusion instrument according to FIG. 1 in the open position.

FIG. 3 shows an enlarged perspective view of an embodiment of a support structure according to the invention, for arrangement in the head area of the tissue fusion instrument according to FIG. 2.

FIG. 4 shows a perspective view of a further embodiment of a support structure according to the invention.

FIG. 5 shows a plan view of the support structure according to FIG. 4.

FIG. 6 shows a sectional view of the support structure according to FIGS. 4 and 5.

FIG. 12 shows a schematic view of the head area of the tissue fusion instrument according to FIG. 2, with a further embodiment of a support structure according to the invention which is inserted between the tissue sections to be connected to each other.

FIG. 13 shows a schematic view of the head area of the tissue fusion instrument according to FIG. 2, with a further embodiment of a support structure according to the invention which has a polygonal shape and is insertable between the tissue sections.

FIG. 14 shows a further schematic view of the head area of the tissue fusion instrument according to FIG. 2, similar to FIGS. 12 and 13, wherein a further embodiment of a support structure according to the invention is inserted between an anvil part and a base part of the head area and has a shape-change structure.

FIG. 15 shows the configuration according to FIG. 14, with a schematic view of how the support structure has changed shape.

FIG. 16 shows a schematic view of a further embodiment of a tissue fusion instrument according to the invention, with a support structure which externally encloses the tissue sections.

FIG. 17 experiences a change of shape in the manner of a heat-shrink sleeve.

Figure 7:
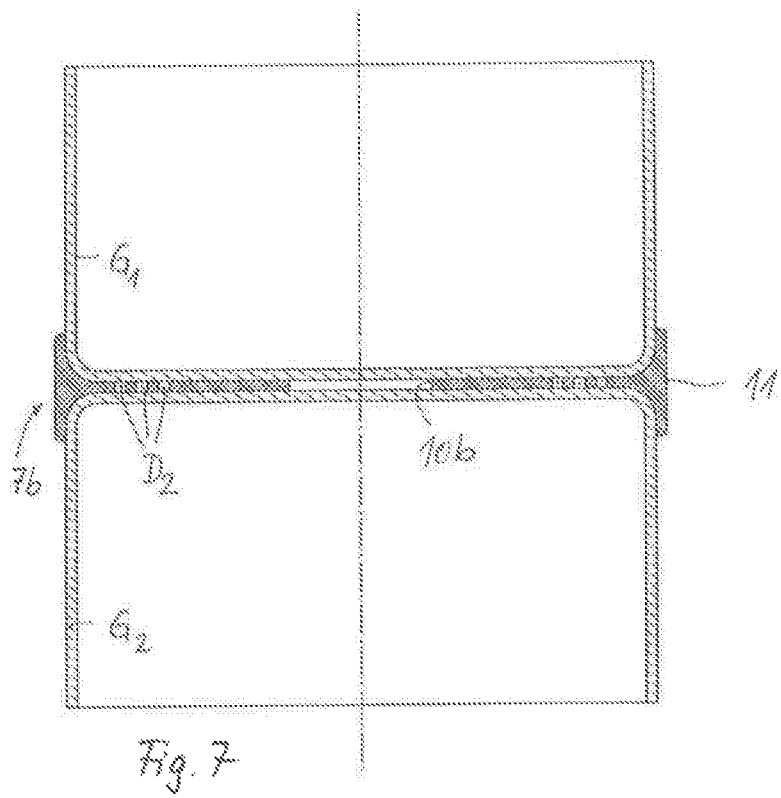
FIG. 7 shows a schematic sectional view of the inclusion of the support structure according to FIGS. 4 to 6 between two biological tissue sections after a tissue fusion procedure using the tissue fusion instrument according to FIGS. 1 and 2.
Figure 8:
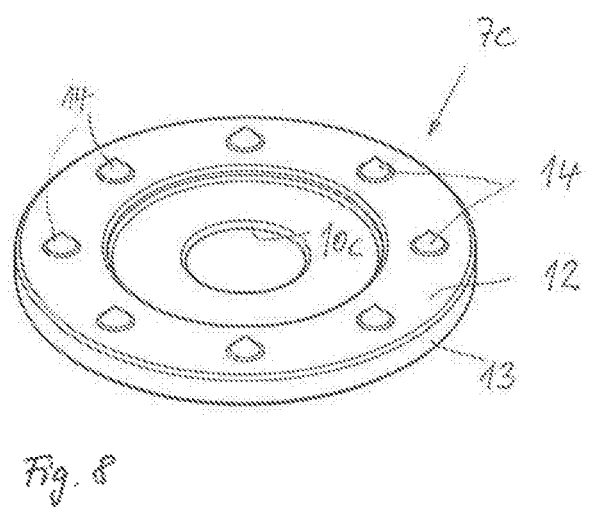
FIG. 8 shows a perspective view of a further embodiment of a support structure according to the invention.
Figure 9:
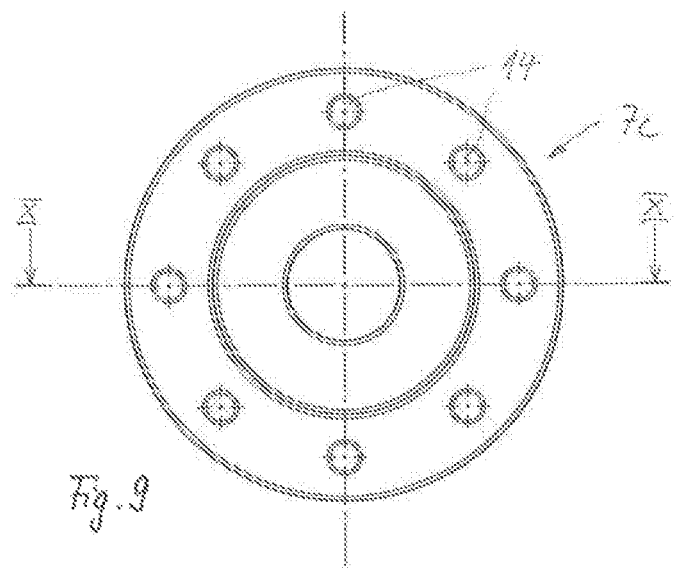
FIG. 9 shows a plan view of the support structure according to FIG. 8.
Figure 10:
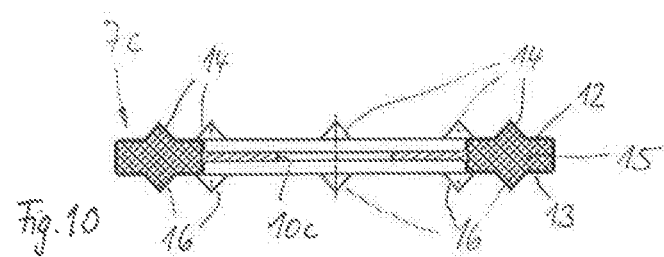
FIG. 10 shows a sectional view, along section line X-X, of the support structure according to FIGS. 8 and 9.
Figure 11:
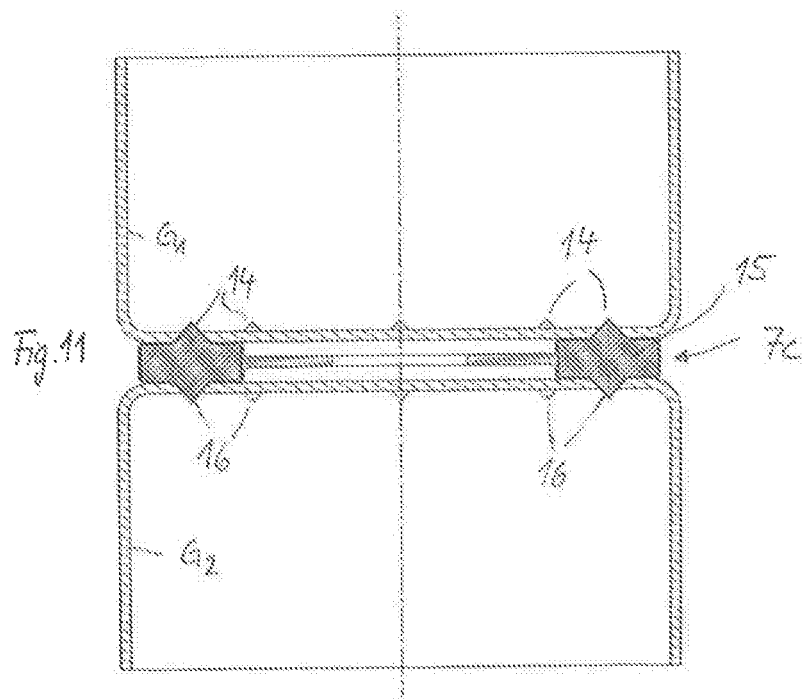
FIG. 11 shows a schematic sectional view of the inclusion of the support structure according to FIGS. 8 to 10 between two tissue sections to be connected to each other using a tissue fusion instrument according to FIGS. 1 and 2.

A surgical tissue fusion instrument according to FIGS. 1 to 17 is designed as a circular tissue fusion instrument 1. The tissue fusion instrument 1 has a grip area (not shown in any detail) which can be grasped by hand in order to operate the tissue fusion instrument. The grip area is assigned an actuation handle 5, which permits activation and control of the tissue fusion instrument 1. The tissue fusion instrument 1 is supplied with current by a power cable designated by reference sign 4. Alternatively, the tissue fusion instrument 1 can be supplied with current by means of an accumulator. The use of an accumulator has the particular advantage of permitting the installation of an energy source, in particular a high-frequency current generator, into the surgical tissue fusion instrument 1. In this case, the energy source and the accumulator are preferably integrated in the grip area of the surgical tissue fusion instrument 1. A head area of the tissue fusion instrument 1 protrudes from the grip area via an elongate neck and has a base part 2 and an anvil part 3. The anvil part 3 is mounted longitudinally displaceably in the base part 2 by means of an anvil shaft 6 coaxial to a central longitudinal axis M of the neck of the head area. By means of a drive system (not shown in any detail), the anvil part 3 can travel relative to the base part 2 along the central longitudinal axis M between an open position (FIG. 2) and a closed position (FIG. 1). The base part 2 and the anvil part 3 have end faces which are directed toward each other and which form contact faces by which biological tissue sections to be connected to each other are grasped and brought together. The anvil part 3 and the base part 2 both define a gripping structure within the meaning of the invention.

The two end faces of the base part 2 and of the anvil part 3 are provided with electrode arrangements 8, 9 which, as heat-generating means, are acted upon electrically and thus, by way of high-frequency electromagnetic waves, apply heat to the biological tissue sections that are to be connected to each other. The contact area defined between the contact faces of the base part 2 and of the anvil part 3 in the closed position is designated as connection area or as connection site for the tissue sections. The electrode arrangements 8, 9 permit a focused and directional application of energy to the connection area, such that a high level of heat can be introduced into the tissue sections to be connected to each other and can bring about a desired tissue fusion between the tissue sections. This results in a cohesive connection between the tissue sections, which connection can be assisted or strengthened mechanically by additional mechanical connecting means such as staples or the like. The circular tissue fusion instrument 1 is able in particular to connect biological tissue sections that are formed as hollow organs.

To aid and promote the connection between the tissue sections, the head area of the tissue fusion instrument 1 is additionally assigned a support structure 7, 7a to 7g, which has an at least substantially rotationally symmetrical design and coaxially surrounds the central longitudinal axis M of the head area. The support structure 7 according to FIG. 2 is simply a schematic view in the manner of a placeholder for the support structures 7a to 7g shown in detail in FIGS. 3 to 17. The schematically depicted support structure 7 shows the arrangement of the support structures 7a to 7f in the head area of the tissue fusion instrument 1.

All the embodiments of support structures 7, 7a to 7g are made from a medically compatible material, or have such a material, and are dimensionally stable in an unloaded initial state with the tissue fusion instrument 1 opened according to FIG. 2. Each of the support structures 7, 7a to 7g serves to promote and aid the tissue fusion between the tissue sections $G_1$, $G_2$. All of the support structures 7a to 7g have a physical functional structure, in particular an additional physical functional structure. In the embodiments according to FIGS. 3 to 11, the physical functional structure is formed by mechanical functional sections. All of the support structures 7, 7a to 7g are preferably made of a resorbable material or have such a material.

The support structure 7a according to FIG. 3 has apertures $D_1$ extending along arcs of a circle and distributed uniformly about the circumference of the support structure 7a. The support structure 7a is disk-shaped and has a central receiving eye 10a, which serves to mount the support structure 7a on the anvil shaft 6 of the anvil part 3. The apertures $D_1$ are positioned flush with the electrode arrangements 8 and 9 of the anvil part 3 and of the base part 2 and are accordingly located at the sites of the greatest input of energy. During tissue fusion, the tissue sections $G_1$, $G_2$ are connected to each other through the apertures $D_1$, thereby sandwiching the support structure 7a between them.

In the embodiment according to FIG. 4, the support structure 7b likewise has apertures $D_2$ which, in this embodiment, are designed as perforations. The apertures $D_2$ also designed as perforations extend about a circumference of the support structure 7b, which is designed as an annular disk. The support structure 7b has a receiving eye 10b analogously to the above-described support structure 7a. The apertures $D_2$ are distributed uniformly in the shape of a circle about the circumference of the support structure 7b and are arranged flush with the electrode arrangements 8, 9, so as to be able to obtain, in the area of the highest input of energy, a particularly good connection between the tissue sections $G_1$, $G_2$. The support structure 7b is additionally provided with an edge web 11, which is formed integrally on the outer periphery of the disk-shaped support structure 7b and protrudes axially, with respect to a radial plane of the support structure 7b, on opposite sides relative to a disk surface of the support structure 7b. After tissue fusion has taken place, the edge web 11 flanks the tissue sections $G_1$, $G_2$ radially to the outside in the area of the connection site between the tissue sections $G_1$, $G_2$. The edge web 11 accordingly contributes to stiffening and supporting the connection site between the tissue sections G1, G2. It will be seen from FIG. 7 that the support structure 7b is sandwiched between the tissue sections $G_1$, $G_2$, which are in the form of hollow organs. Radially with respect to an imaginary central longitudinal axis of the mutually aligned tissue sections $G_1$, $G_2$ formed as hollow organs, the connection site extends as a planar connection in the area of the radial plane predefined by the support structure 7b.

The support structure 7c according to FIGS. 8 to 11 is likewise disk-shaped, with a central receiving eye 10c for mounting on the anvil shaft 6 of the anvil part 3. On its opposite end faces, the support structure 7c has, as additional physical functional structures, profiles 14, 16 which protrude axially outward in the form of humps from the end face. The profiles 14, 16 protrude outward from the opposite end faces of the support structure 7c.

The support structure 7c is constructed from two annular shells 12 and 13, which are tightly connected to each other at their edge areas. A storage space 15 for accommodating a liquid or flowable additive is provided between the annular shells 12 and 13 and serves to aid or promote tissue fusion in the area of the connection site between the tissue sections $G_1$, $G_2$. The liquid or flowable additive is medically compatible and can in particular have properties of adhesion or properties that promote wound-healing.

The end walls and side walls of the annular shells 12, 13 surrounding the storage space 15 are designed in such a way that they are able to burst or tear open when a pressure load is applied to the end faces. In this way, the additive is freed and is able to spread out in the area of the connection site between the tissue sections $G_1$, $G_2$. The profiles 14, 16 deform when pressure is applied during closure of the head area of the tissue fusion instrument 1 and aid the tearing open or bursting open of the walls of the storage space 15.

In the embodiment according to FIG. 12, the support structure 7e in the head area of the tissue fusion instrument is beaker-shaped and has a disk-shaped area, extending radially with respect to a central longitudinal axis of the head area, and an axially extending annular wall, which surrounds the outside of the base part 2 and the associated tissue section $G_2$. The material of the beaker-shaped support structure 7e is electrically conductive at least in parts. It is used as a positive pole 20 for a corresponding application of heat to the tissue sections $G_1$, $G_2$ by means of electrical energy, whereas the electrode arrangements 8 and 9 are controlled as negative pole 19.

In the embodiment according to FIG. 13, the support structure 7f, starting from a disk-shaped initial state analogous to FIG. 2, has already been deployed into a three-dimensional, polygonal shape-change state. For this purpose, the support structure 7f preferably has a shape-memory material, which is activated in particular by application of temperature, electrical energy or moisture. The shape into which the support structure 7f can deploy is dependent in particular on the use that is intended. In the deployed form, the support structure can either bear internally on the tissue sections $G_1$, $G_2$ or enclose these on the outside in the area of the connection site.

In the embodiment according to FIGS. 14 and 15, the support structure 7d, in an initial state, is provided as a two-part annular disk with a first ring part 17 and a second ring part 18, which are joined flat onto each other in the radial plane. The support structure 7d is also provided with a shape-change property, wherein the two parts 17 and 18, after activation, deploy into oppositely directed beaker-shaped or sleeve-shaped forms, as can be seen from FIG. 15. In their shape-changed state, the parts 17 and 18 radially enclose the outside of the tissue sections $G_1$, $G_2$ via their ring walls along a defined axial length, such that the support structure 7d, in addition to defining a radial surface connection to the tissue sections $G_1$, $G_2$ in the area of the radial connection site, also defines an external jacket along a defined axial length.

In the embodiment according to FIGS. 16 and 17, the support structure 7g has a tubular configuration and radially surrounds the outside of the tissue sections $G_1$, $G_2$ and the head area of the tissue fusion instrument. The support structure 7g is also provided with a shape-change structure. Activated by a physical or chemical environmental parameter, in particular by temperature application, the shape-change structure is shrunk from an initial state (FIG. 16) in the connection area between the anvil part 3 and the base part 2, as a result of which an annular constriction 21 forms, which is pressed axially between the tissue sections $G_1$, $G_2$ when anvil part 3 and base part 2 are brought together.

The invention claimed is:

1. A surgical tissue fusion instrument with two gripping structures which are movable relative to each other and which are designed to bring together biological tissue sections ($G_1$, $G_2$) that are to be connected to each other, with heat-generating means which are assigned to the gripping structures and, during tissue fusion, cause heat to be introduced in the area of a connection site of the biological tissue sections ($G_1$, $G_2$), and also with a support structure which is assigned to the gripping structures and, during tissue fusion, is operatively connected to the tissue sections ($G_1$, $G_2$), wherein the support structure has opposite end faces and at least one additional physical functional structure for aiding or promoting the tissue fusion, wherein the physical functional structure has profiles in the form of angular protuberances or indentations, which are provided on at least one end face of the opposite end faces of the support structure directed toward a gripping structure wherein the support structure is constructed from two annular shells, which are connected to each other at their edge areas, and wherein a storage space for accommodating a liquid or flowable additive is provided between the annular shells, and wherein end walls and side walls of the annular shells surround the storage space, wherein the end walls and side walls of the annular shells are designed in such a way that they are able to burst or tear open when a pressure load is applied to the end faces of the support structure.

2. The surgical tissue fusion instrument of claim 1, wherein the physical functional structure has apertures or material weakenings in the support structure which are positioned in areas where the heat introduced by the heat-generating means passes through the support structure and the tissue sections ($G_1$, $G_2$).

3. The surgical tissue fusion instrument of claim 2, wherein the apertures are designed as linearly extending or circularly extending oblong holes.

4. The surgical tissue fusion instrument of claim 2, wherein the apertures are designed as perforations.

5. The surgical tissue fusion instrument of claim 1, wherein the storage space serves to aid tissue fusion in the area of the connection site between the tissue sections (G1, G2).

6. The surgical tissue fusion instrument of claim 1, wherein the storage space is integrated in the support structure.

7. The surgical tissue fusion instrument of claim 1, wherein the physical functional structure is designed to be electrically conductive at least in parts.

8. The surgical tissue fusion instrument of claim 7, wherein the physical functional structure is designed as an electrical pole for electrical activation of the energy input by the heat-generating means.

9. The surgical tissue fusion instrument of claim 1, wherein the physical functional structure is formed by a shape-change structure, which can be activated according to a change of at least one physical or chemical environmental parameter.

10. The surgical tissue fusion instrument of claim 9, wherein a change of temperature and/or change of water content acting on the functional structure is provided as the change of environmental parameters.

* * * * *